United States Patent [19]

Kitano et al.

[11] Patent Number: 5,053,162

[45] Date of Patent: Oct. 1, 1991

[54] DIFLUOROALKYLCYCLOHEXYLBEN-ZONITRILE DERIVATIVE

[75] Inventors: Kisei Kitano; Yasuyuki Goto; Manabu Uchida; Makota Ushioda, all of Chibaken, Japan

[73] Assignee: Chisso Corporation, Osakafu, Japan

[21] Appl. No.: 508,415

[22] Filed: Apr. 13, 1990

[30] Foreign Application Priority Data

Apr. 13, 1989 [JP] Japan .................................... 1-94141

[51] Int. Cl.$^5$ ........................ C09K 19/43; C09K 19/00
[52] U.S. Cl. ............................ 252/299.61; 252/299.6; 252/299.63; 570/185
[58] Field of Search ...................... 252/299.01, 299.61, 252/299.63, 299.6, 299.66; 570/127, 128, 182, 185

[56] References Cited

U.S. PATENT DOCUMENTS 4,130,502 12/1978 Eidenschink et al. ............. 252/299
4,726,911 2/1988 Krause et al. .................. 252/299.61
4,880,562 11/1989 Kitano et al. .................. 252/299.63

Primary Examiner—Robert L. Stoll
Assistant Examiner—Greg M. Sweet
Attorney, Agent, or Firm—Wenderoth, Lind & Ponack

[57] ABSTRACT

A liquid crystalline compound having a small $\Delta n$ value; suitable for preparing a liquid crystal display element having a broad viewing angle; having a large positive $\Delta\epsilon$ value; and suitable for preparing a liquid crystal composition having a low driving voltage for liquid crystal display devices, and a liquid crystal composition containing the compound are provided, which compound is expressed by the formula

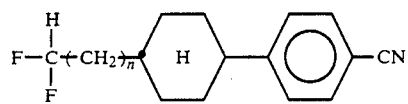

wherein n represents an integer of 0 to 20.

3 Claims, No Drawings

DIFLUOROALKYLCYCLOHEXYLBENZONITRILE DERIVATIVE

BACKGROUND OF THE INVENTION

This invention relates to a novel liquid crystalline compound useful for display elements, and a liquid crystal composition containing the compound.

Liquid crystal substances and compositions thereof have been used for various display devices, making use of the dielectric anisotropy (hereinafter abbreviated to $\Delta\epsilon$) and the optical anisotropy (hereinafter abbreviated to $\Delta n$) in the liquid crystal phases of the above substances and compositions.

Liquid crystal display modes include electrically controlled birefringence mode (ECB mode), twisted nematic mode (TN mode), supertwisted birefringence effect mode (SBE mode), dynamic scattering mode (DS mode), guest-host mode, etc., corresponding to the electrooptical effect applied. Liquid crystal materials used for display devices should be provided with a combination of various characteristics such as a broad mesomorphic range, a low viscosity, a large positive $\Delta\epsilon$ value or negative $\Delta\epsilon$ value, no large change in various characteristics of display elements, particularly in the threshold voltage, over a broad temperature range, etc., depending on the display modes and also depending on various characteristics required for display elements.

At present, however, there is no single compound which is practically usable in the aspect of mesomorphic range, operating voltage and response properties. Thus, a mixture of several kinds of liquid crystal compounds, or a mixture of several kinds of liquid crystal compounds with a potentially liquid crystalline compound or a non-liquid crystal compound have been practically used.

SUMMARY OF THE INVENTION

The object of the present invention is to provide a liquid crystalline compound and a liquid crystal composition usable for liquid crystal display devices. The liquid crystalline compound referred to herein means not only compounds exhibiting liquid crystal phases but also compounds which usually exhibit no liquid crystal phase but effectively function in a certain aspect of liquid crystal behavior when dissolved in other liquid crystal compounds.

The present invention resides in a compound expressed by the formula

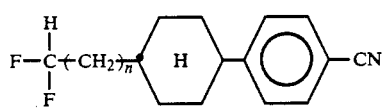 (I)

wherein n represents an integer of 0 to 20, and a liquid crystal composition containing at least one such compound.

DETAILED DESCRIPTION OF PREFERRED EMBODIMENTS

Preferably, n is an integer of 0 to 7.

Concrete examples of the compound of the formula (I) of the present invention are as follows:

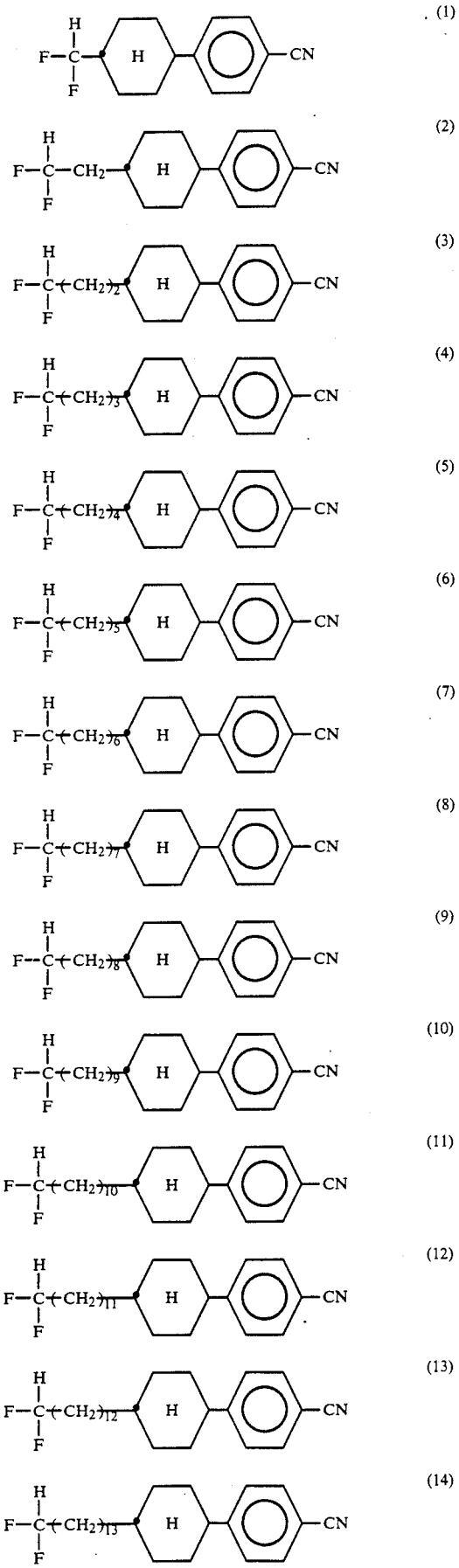

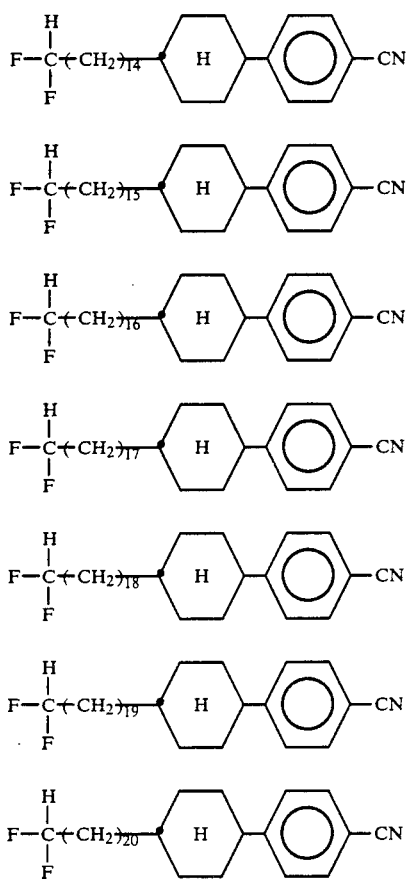

The compound of the formula (I) of the present invention is a liquid crystalline compound. Further, the compound of the present invention has a small Δn value, and is also suitable for preparing a liquid crystal display element having a broad viewing angle. Further, the compound of the present invention has a large positive Δε value and also affords a liquid crystal composition suitable for display devices operated at low driving voltages.

Further, the compound of the present invention has good stability to heat, light, electricity, air, moisture, etc., required for liquid crystal display materials, and also has a superior compatibility with other existing liquid crystalline compounds such as ester compounds, Schiff's base compounds, ethane compounds, acetylene compounds, azoxy compounds, biphenyl compounds, cyclohexane compounds, pyrimidine compounds, pyridine compounds, etc. so that when the compound is mixed with these compounds or mixtures thereof, it is possible to obtain a liquid crystal material suitable to various use applications.

As liquid crystal components used for the liquid crystal composition of the present invention besides the compound of the formula (I), for example, liquid crystal compounds expressed by the following formulas (i) to (xxxiii) are preferred:

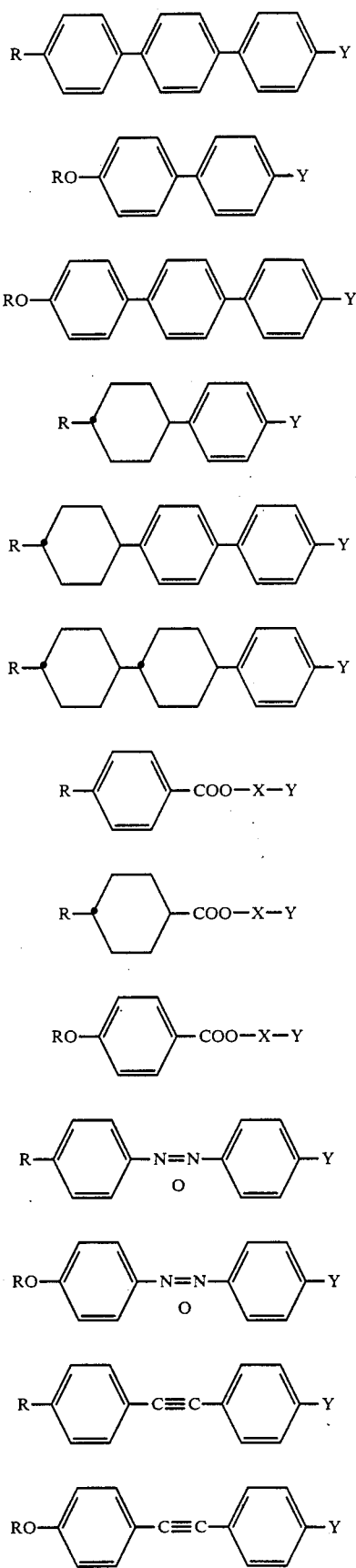

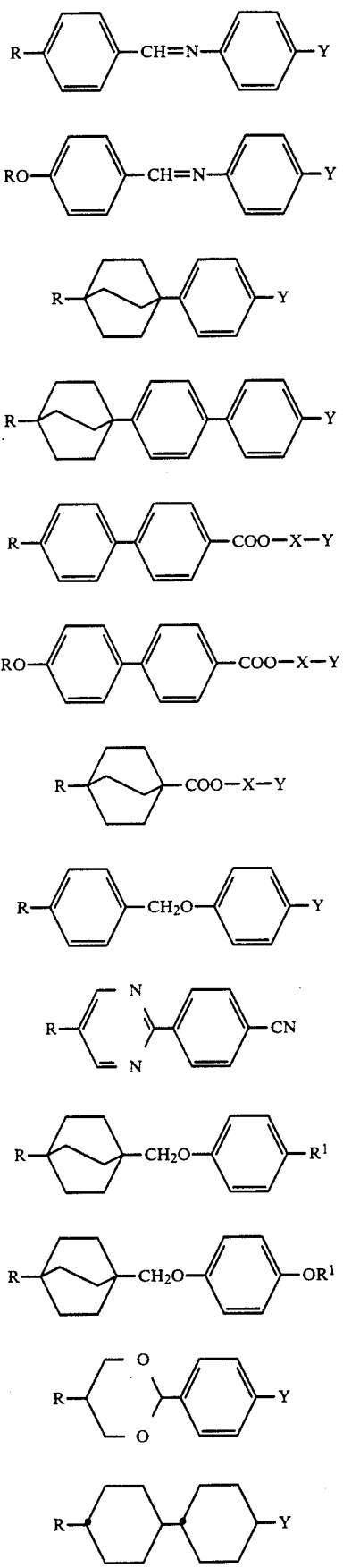
In the formulas (i)–(xxxiii), X represents
Y represents —CN, a halogen atom or $OR^1$; R and $R^1$ each represent an alkyl group; and the hydrogen atoms of the above
may be replaced by halogen atom(s).
The compound of the present invention may be prepared for example in the following manner;

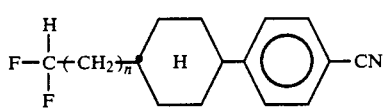 (I)

In the above formulas, n is as defined above.

Namely, when an aldehyde derivative (II) obtained in a manner as described later and corresponding to the objective product is subjected to fluorine-substitution reaction with diethylaminosulfur trifluoride in dichloromethane, followed by subjecting the reaction product to separation and purification operations usually carried out, such as vacuum distillation, chromatography, recrystallization, etc., then it is possible to obtain the objective compound (I).

The aldehyde derivative (II) used as the raw material for the product may be prepared for example in the following manner:

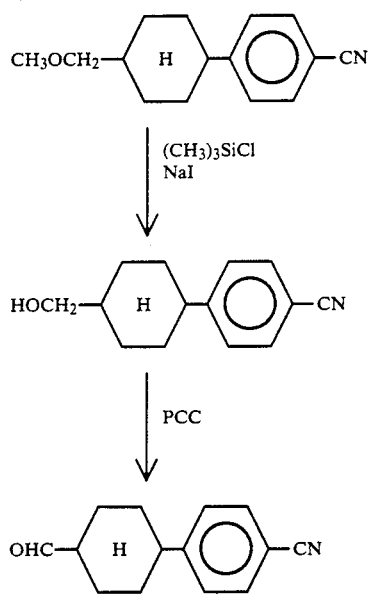

Namely, known trans-4-methoxymethyl-1-(4-cyanophenyl)-cyclohexane (III) (for example obtained according to a method disclosed in Japanese patent application laid-open No. Sho 58-59956) is reacted with trimethylsilyl chloride and sodium iodide in a solvent of acetonitrile according to a method disclosed in J. Org. Chem., 44, 1247 (1979) to obtain trans-4-(4-cyanophenyl)cyclohexylcarbinol (IV), followed by oxidizing this compound (IV) with pyridinium chlorochromate (PCC) into an aldehyde according to the method disclosed in Synthesis, 245 (1982) to obtain trans-4-(4-cyanophenyl)cyclohexylcarbaldehyde (V). This compound (V) corresponds to the above aldehyde derivative (II) wherein n=0. Further, compounds corresponding to the aldehyde (II) wherein n represents an integer of 1 to 20 may be prepared for example according to the following method:

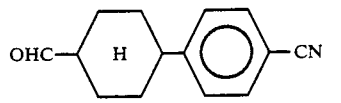 (V)

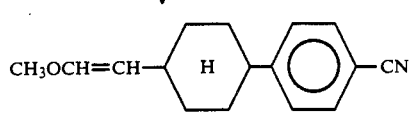 (VI)

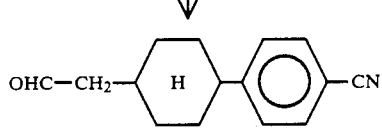 (VII)

Namely, methoxymethyltriphenylphosphonium chloride and a base (such as sodium t-butoxide, sodium methylate, phenyllithium, n-butyllithium, etc.) are reacted with the aldehyde derivative (V) according to Wittig's reaction, to obtain a methoxyvinyl derivative (VI), followed by heating this compound (VI) under an acidic condition (for example heating it with hydrochloric acid in a solvent of tetrahydrofuran) to obtain an aldehyde (VII) having one more methylene group as compared with the original aldehyde (V). When the above Wittig's reaction and acid treatment reaction are successively n applied times to the aldehyde derivative (V), it is possible to obtain an aldehyde derivative (II) wherein n represents one or more.

The present invention will be described in more detail by way of Examples, but it should not be construed to be limited thereto.

Example 1

Preparation of trans-1-difluoromethyl-4-(4-cyanophenyl)cyclohexane (a compound of the formula (I) wherein n=0, i.e. compound (1))

(i) Preparation of trans-4-(4-cyanophenyl)cyclohexanecarbaldehyde

Trimethylsilyl chloride (305.6 g, 2.81 mol) was dropwise added to trans-4-methoxymethyl-1-(4-cyanophenyl)-cyclohexane (III) (322.5 g, 1.41 mol), sodium iodide (421.6 g, 2.81 mol) and acetonitrile (2.5 l) in nitrogen atmosphere with stirring at 35° C. over 30 minutes, followed by agitating the mixture for 20 minutes, cooling the reaction mixture down to 10° C., filtering it by suction, pouring the filtrate in ice water (2 Kg), extracting with chloroform (1.5 l), twice washing the resulting chloroform solution with a 10% by weight aqueous solution of sodium thiosulfate (0.5 l), three times washing with water (1 l), distilling off chloroform from the chloroform solution and three times recrystallizing the residue from toluene (300 m) for purification to obtain trans-4-(4-cyanophenyl)cyclohexylcarbinol (IV) (182.5 g, 0.848 mol) having a m.p. of 108.5°–110.8° C. On the other hand, pyridinium chlorochromate (161.7 g, 0.750 mol) was added to dichloromethane (1 l), followed by instantaneously adding to the mixture, a solution of trans-4-(4-cyanophenyl)cyclohexylcarbinol (IV) (107.6 g, 0.500 mol) obtained above, in dichloromethane (0.7 l) with stirring at room temperature, further agitating the mixture at room temperature for 1.5 hours, adding diethyl ether (1 l) to the reaction mixture, and concentrating the supernatant by passing it through a Florisil chromatography column to obtain trans-4-(4-cyanophenyl)-cyclohexylcarbaldehyde (V) (101.2 g, 0.474 mol).

(ii) Preparation of the captioned compound

A solution of trans-4-(4-cyanophenyl)cyclohexylcarbaldehyde (V) (15.0 g, 0.070 mol) obtained in (i), in dichloromethane (90 ml) was dropwise added to a solution of commercially available diethylaluminosulfur trifluoride (13.6 g, 0.084 mol) in dichloromethane (40 ml), under cooling in ice bath, with stirring, in nitrogen gas current over 30 minutes, further agitating the mixture for one hour, gradually dropwise adding water (100 ml) under cooling in an ice bath, washing the resulting oily layer with water, further washing with a saturated aqueous solution of sodium hydrogen carbonate, further washing with water till the aqueous layer became neutral, drying the oily layer over anhydrous magnesium sulfate, separating the drying agent, distilling off dichloromethane, dissolving the residue in toluene, purifying according to column chromatography using alumina, repeatedly recrystallizing and drying to obtain the objective compound (7.1 g, 0.030 mol) having a m.p. of 54.6° C.

Example 2

Preparation of trans-1-(2,2-difluoroethyl)-4-(4-cyanophenyl)cyclohexane (a compound of the formula (I) wherein n=1 i.e. compound (2))

(i) Preparation of trans-4-(4-cyanophenyl)cyclohexylacetaldehyde (VII)

Commercially available methoxymethyltriphenylphosphonium chloride (127.5 g, 0.372 mol) was added to methyl t-butyl ether (1 l), followed by adding potassium t-butoxide (43.1 g, 0.384 mol) in argon atmosphere with stirring at −10° C. over 10 minutes, agitating the reaction mixture at 0° C. for one hour, dropwise adding a solution of trans-4-(4-cyanophenyl)cyclohexylcarbaldehyde (V) (44.1 g, 0.207 mol) obtained in Example 1, (i), in methyl t-butyl ether (200 ml) at −10° C. over 15 minutes, agitating the reaction mixture at 0° C. for one hour, adding toluene (0.3 l) and water (0.3 l), four times washing the resulting toluene solution with water (0.3 l), drying over anhydrous sodium sulfate, separating the drying agent, distilling off toluene, dissolving the residue in ethyl acetate (100 m() on heating, allowing the solution to stand still at room temperature for one day, filtering off deposited crystals, concentrating the filtrate, dissolving the concentrate in heptane, purifying the solution according to silica gel column chromatography to obtain trans-1-(2-methoxy-1-ethenyl)-4-(4-cyanophenyl)cyclohexane (39.8 g, 0.165 mol), adding to the total quantity of this compound, tetrahydrofuran (500 ml) and 2N-hydrochloric acid (120 ml), heating the mixture under reflux with stirring for one hour, cooling the resulting material, adding toluene (300 ml) and water (1 l) to the reaction solution for washing, three times washing the resulting toluene solution with water (1 l), drying over anhydrous sodium sulfate, separating the drying agent and distilling off toluene, to obtain trans-4-(4-cyanophenyl)cyclohexylacetaldehyde (VII) (35.4 g, 0.156 mol).

(ii) Preparation of the captioned compound

Using trans-4-(4-cyanophenyl)cyclohexylacetaldehyde (VII) obtained in (i) as a raw material, the captioned compound was obtained in the same manner as in Example 1, (ii). M.P.: 57.2° C.

Example 3

7 Preparation of trans-1-(3,3-difluoropropyl)-4-(4-cyanophenyl)cyclohexane (a compound of the formula (I) wherein n=2, i.e. compound (3))

(i) Preparation of 3-[trans-4-(4-cyanophenyl)cyclohexyl]-1-propanal

Commercially available methoxymethyltriphenylphosphonium chloride (15.7 g, 0.0458 mol) was added to tetrahydrofuran (100 ml), followed by dropwise adding a 25% by weight solution of phenyllithium in toluene 23 ml) in argon atmosphere with stirring at −10° C. over 10 minutes, agitating the reaction mixture at 0° C. for 30 minutes, dropwise adding a solution of trans-4-(4-cyanophenyl)cyclohexylacetaldehyde (VII) (7.3 g, 0.032 mol) obtained in Example 2 (i), in tetrahydrofuran (90 ml) at −10° C. over 10 minutes, agitating the reaction mixture at 0° C. for 2 hours, adding toluene (100 ml) and water (200 ml) for washing, three times washing the resulting toluene solution with water (200 ml), drying over anhydrous sodium sulfate, separating the drying agent, distilling off toluene, dissolving the residue in ethyl acetate (20 ml) on heating, allowing the solution to stand still at room temperature for one day, filtering off deposited crystals, concentrating the mother liquor, dissolving the concentrate in heptane, purifying the solution according to silica gel column chromatography to obtain trans-1-(3-methoxy-2-propenyl)-4-(4-cyanophenyl)cyclohexane (4.4 g, 0.017 mol), adding to the total quantity of this compound, tetrahydrofuran (70 ml) and 2N-hydrochloric acid (18 ml), heating the mixture under reflux with stirring for one hour, cooling the resulting reaction mixture, adding diethyl ether (50 ml) and water (50 ml) to the reaction mixture, three times washing the resulting diethyl ether solution with water (50 ml), drying over anhydrous sodium sulfate, separating the drying agent and distilling off diethyl ether to obtain 3-[trans-4-(4-cyanophenyl)cyclohexyl]-1-propanal (4.2 g, 0.017 mol).

(ii) Preparation of the captioned compound

Using 3-[trans-4-(4-cyanophenyl)cyclohexyl]-1-propanal obtained in (i) as a raw material, the captioned compound was obtained in the same manner as in Example 1 (ii).

This compound exhibited a m.p. of 40.7° C. and an NI point of 9.7° C.

Example 4

Preparation of trans-1-(4,4-difluorobutyl)-4-(4-cyanophenyl)cyclohexane (a compound of the formula (I) wherein n=3, i.e. compound (4))

(i) Preparation of 4-[trans-4-(4-cyanophenyl)-cyclohexyl]1-butanal

Commercially available methoxymethyltriphenylphosphonium chloride (257 g, 0.75 mol) was added to tetrahydrofuran (500 ml), followed by adding potassium t-butoxide (84.2 g, 0.75 mol) in argon atmosphere with stirring at −10° C. over 40 minutes, agitating the reaction solution at 0° C. for one hour, dropwise adding a solution of 3-[trans-4-(4-cyanophenyl)cyclohexyl]-1-propanal (121 g, 0.50 mol) obtained according to the method of Example 3 (i), in tetrahydrofuran (400 ml) at −10° C. over one hour, agitating the reaction mixture at 0° C. for one hour, further agitating at 20° C. for 2 hours, adding toluene (1 l) and water (1 l) to the reaction mixture at 0° C., four times washing the resulting toluene solution with water (1 l), drying over anhydrous magnesium sulfate, separating the drying agent, distilling off toluene, purifying the resulting residue according to silica gel column chromatography using heptane as an eluent to obtain trans-1-(4-methoxy-3-butenyl)-4-(4-cyanophenyl)cyclohexane (110.8 g, 0.41 mol), adding to the total quantity of this compound, tetrahydrofuran (1.5 l) and 2N-hydrochloric acid (0.4 l), heating the mixture under reflux, with stirring for one hour, cooling the resulting reaction mixture, adding diethyl ether (0.5 l) and water (1 l), three times washing the resulting diethyl ether solution with water (0.5 l), drying over anhydrous magnesium sulfate, separating the drying agent, concentrating under reduced pressure to obtain a residue (120 g), and recrystallizing from a mixed solvent of heptane and ethyl acetate (3:1) to obtain 4-[trans-4-(4-cyanophenyl)cyclohexyl]-1-butanal (93.0 g, 0.36 mol).

(ii) Preparation of the captioned compound

Using 4-[trans-4-(4-cyanophenyl)cyclohexyl]-1-butanal obtained in (i), as a raw material, the captioned compound was obtained in the same manner as in Example 1, (ii).

This product exhibited a m.p. of 47.5° C. and an NI point of 15.2° C.

Example 5

Preparation of trans-1-(5,5-difluoropentyl)-4-(4-cyanophenyl)cyclohexane (a compound of the formula (I) wherein n=4, i.e. compound (5))

(i) Preparation of 5-[trans-4-(4-cyanophenyl)cyclohexyl]-1-pentanal

Commercially available methoxymethyltriphenylphosphonium chloride (120.8 g, 0.35 mol) was added to tetrahydrofuran (400 ml), followed by adding potassium t-butoxide (39.5 g, 0.35 mol) in argon atmosphere with stirring at −10° C. over 20 minutes, agitating the reaction mixture at 0° C. for one hour, dropwise adding a solution of 4-[trans-4-(4-cyanophenyl)cyclohexyl]-1-butanal (60.0 g, 0.23 mol) obtained according to the method of Example 4 (i), in tetrahydrofuran (300 ml) at −10° C. over one hour, agitating the reaction mixture at 0° C. for one hour, further agitating at 20° C. for 2 hours, adding toluene (1 l) and water (1 l) to the reaction mixture at 0° C., 4 times washing the resulting toluene solution with water (1 l), drying over anhydrous magnesium sulfate, separating the drying agent, distilling off toluene, purifying the residue according to silica gel column chromatography using heptane as an eluent to obtain trans-1-(5-methoxy-4-pentenyl)-4-(4-cyanophenyl)cyclohexane (52.6 g, 0.19 mol), adding to the total quantity of this compound, tetrahydrofuran (750 ml) and 2N-hydrochloric acid (190 ml), heating the mixture under reflux with stirring for one hour, cooling the resulting solution, adding diethyl ether (0.5 l) and water (1 l) to the reaction mixture, three times washing the resulting diethyl ether solution with water (0.5 l), drying over anhydrous magnesium sulfate, separating the drying agent, concentrating under reduced pressure, recrystallizing the resulting residue (50 g) from a mixed solvent of heptane and ethyl acetate (3:1), and drying to obtain 5-[trans-4-(4-cyanophenyl)cyclohexyl]-1-pentanal (43.1 g, 0.16 mol).

(ii) Preparation of the captioned compound

Using 5-[trans-4-(4-cyanophenyl)cyclohexyl]-1-pentanal as a raw material, the captioned compound was obtained in the same manner as in Example 1 (ii).

This compound exhibited a CN point of 29.0° C. and an NI point of 34.3° C.

Example 6 (Use example 1)

A liquid crystal composition A consisting of

| | |
|---|---|
| $C_3H_7$—(H)—(O)—CN | 24 wt. parts |
| $C_5H_{11}$—(H)—(O)—CN | 36 wt. parts |
| $C_7H_{15}$—(H)—(O)—CN | 25 wt. parts and |
| $C_5H_{11}$—(H)—(O)—(O)—CN | 15 wt. parts | exhibited an NI point of 72.0° C., a viscosity at 20° C. $\eta_{20}$ of 27.5 cp, a $\Delta\epsilon$ of 11.0 ($\epsilon_{//}=15.7$ and $\epsilon_\perp=4.7$) and a $\Delta n$ of 0.137, and when the composition was filled in a TN cell of 9 μm thickness, the threshold voltage was 1.83 V. When trans-1-difluoromethyl-4-(4-cyanophenyl)-cyclohexane (15 parts by weight) obtained in Example 1 was added to the liquid crystal composition A (85 parts by weight), the resulting liquid crystal composition exhibited an NI point of 56.4° C., a $\eta_{20}$ of 31.3 cp and a $\Delta\epsilon$ of 10.4 ($\epsilon_{//}=15.5$ and $\epsilon_\perp=5.1$) and the $\Delta n$ was lowered to 0.130. When this composition was sealed in the same TN cell of 9 μm thickness as the above, the threshold voltage was 1.59 V, which was a notable reduction in the driving voltage.

Examples 7–10 (Use examples 2–5)

Compounds of the formula (I) obtained in Examples 2–5, each in an amount of 15 parts by weight, were respectively added to the nematic liquid crystal composition A (85 parts by weight) used in Example 6 to prepare liquid crystal compositions. The NI points, $\eta_{20}$ s, $\Delta n$s, $\Delta\epsilon$s and threshold voltages of the resulting liquid crystal compositions are shown in Table 1 together with the results of Example 6.

As described above, when the compound of the formula (I) of the present invention is used as a component of liquid crystals, there is obtained a liquid crystal composition having preferred specific features such as a small $\Delta n$ value, a low driving voltage, etc.

TABLE 1

| Example | Compound used | | NI point (°C.) | $\eta_{20}$ (cp) | $\Delta n$ | $\Delta \epsilon$ | Threshold voltage(V) |
|---|---|---|---|---|---|---|---|
| 6 | F$_2$CH—⬡H—⌬—CN | (1) | 56.4 | 31.3 | 0.130 | 10.4 | 1.59 |
| 7 | F$_2$CH—CH$_2$—⬡H—⌬—CN | (2) | 63.4 | 31.5 | 0.126 | 11.1 | 1.64 |
| 8 | F$_2$CH(CH$_2$)$_2$—⬡H—⌬—CN | (3) | 64.6 | 33.3 | 0.135 | 10.4 | 1.76 |
| 9 | F$_2$CH(CH$_2$)$_3$—⬡H—⌬—CN | (4) | 65.3 | 31.4 | 0.130 | 10.5 | 1.63 |
| 10 | F$_2$CH(CH$_2$)$_4$—⬡H—⌬—CN | (5) | 63.9 | 32.1 | 0.125 | 10.0 | 1.64 |

What we claim is:

1. A compound expressed by the formula

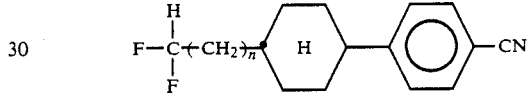

wherein n represents an integer of 0 to 20.

2. A compound according to claim 1 wherein n represents an integer of 0 to 7.

3. A liquid crystal composition comprising at least two components at least one of which is a compound as set forth in claim 1.

* * * * *